(12) United States Patent
Romani et al.

(10) Patent No.: US 8,337,828 B2
(45) Date of Patent: *Dec. 25, 2012

(54) USE OF THYMOSIN ALPHA 1, ALONE OR IN COMBINATION WITH PTX3 OR GANCICLOVIR, FOR THE TREATMENT OF CYTOMEGALOVIRUS INFECTION

(75) Inventors: Luigina Romani, Perugia (IT); Francesco Bistoni, Perugia (IT); Enrico Garaci, Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 171 days.

This patent is subject to a terminal disclaimer.

(21) Appl. No.: 12/298,643

(22) PCT Filed: Apr. 12, 2007

(86) PCT No.: PCT/EP2007/053574
§ 371 (c)(1),
(2), (4) Date: Feb. 27, 2009

(87) PCT Pub. No.: WO2007/128647
PCT Pub. Date: Nov. 15, 2007

(65) Prior Publication Data
US 2009/0275508 A1    Nov. 5, 2009

(30) Foreign Application Priority Data
May 2, 2006  (EP) .................... 06113401

(51) Int. Cl.
*A61K 47/42* (2006.01)
*A61K 38/00* (2006.01)

(52) U.S. Cl. .................... 424/93.1; 530/350
(58) Field of Classification Search .......... None
See application file for complete search history.

(56) References Cited

U.S. PATENT DOCUMENTS

| 5,632,983 | A | 5/1997 | Hadden et al. |
|---|---|---|---|
| 5,939,423 | A | 8/1999 | Karlin et al. |
| 6,001,799 | A | 12/1999 | Chretien et al. |
| 6,106,868 | A | 8/2000 | Mutchnik et al. |
| 7,910,092 | B2 * | 3/2011 | Carminati et al. ........ 424/93.1 |
| 2001/0012830 | A1 | 8/2001 | Horwitz |

FOREIGN PATENT DOCUMENTS

| WO | WO 98/18491 A1 * | 5/1998 |
|---|---|---|
| WO | WO99/32516 A2 * | 7/1999 |
| WO | 00/18417 X | 4/2000 |
| WO | 03/035111 X | 5/2003 |
| WO | 2004/094991 X | 11/2004 |

OTHER PUBLICATIONS

Sjogren M. Journal of Gastroenterology and Hepatology, 2004, vol. 19, pp. S69-S72.*
Mocarski et al. Pro. Natl. Acad. Sci. USA vol. 90, pp. 104-108, 2004.*

* cited by examiner

*Primary Examiner* — Bao Li
(74) *Attorney, Agent, or Firm* — Lucas & Mercanti, LLP (57) ABSTRACT

It is described the use of thymosin alpha 1 in combination with long pentraxin PTX3 or Ganciclovir, for the preparation of a medicament for the prevention or treatment of viral diseases and/or for inhibiting virus activation.

3 Claims, 6 Drawing Sheets

SEQUENCE LISTING

```
<160> NUMBER OF SEQ ID NOS: 4

<210> SEQ ID NO 1
<211> LENGTH: 27
<212> TYPE: PRT
<213> ORGANISM: Artificial Sequence
<220> FEATURE:
<223> OTHER INFORMATION: Synthetic peptide

<400> SEQUENCE: 1

Ser Asp Ala Ala Val Asp Thr Ser Ser Glu Ile Thr Thr Lys Asp Leu
1               5                   10                  15

Lys Glu Lys Lys Glu Val Glu Glu Ala Glu Asn
            20                  25

<210> SEQ ID NO 2
<211> LENGTH: 28
<212> TYPE: PRT
<213> ORGANISM: Artificial Sequence
<220> FEATURE:
<223> OTHER INFORMATION: Synthetic peptide

<400> SEQUENCE: 2

Ala Lys Ser Asp Val Lys Ala Glu Thr Ser Ser Glu Ile Asp Thr Thr
1               5                   10                  15

Glu Leu Asp Glu Lys Val Glu Val Lys Ala Asn Glu
            20                  25

<210> SEQ ID NO 3
<211> LENGTH: 27
<212> TYPE: DNA
<213> ORGANISM: Artificial Sequence
<220> FEATURE:
<223> OTHER INFORMATION: Primer

<400> SEQUENCE: 3
aagcagcaca tccgcaccct gagcgcc                                      27

<210> SEQ ID NO 4
<211> LENGTH: 27
<212> TYPE: DNA
<213> ORGANISM: Artificial Sequence
<220> FEATURE:
<223> OTHER INFORMATION: Primer

<400> SEQUENCE: 4
ccaggcgctc ccggcggccc gctctcg                                      27
```

USE OF THYMOSIN ALPHA 1, ALONE OR IN COMBINATION WITH PTX3 OR GANCICLOVIR, FOR THE TREATMENT OF CYTOMEGALOVIRUS INFECTION

This application is a 371 of PCT/EP2007/053574 filed Apr. 12, 2007, which in turn claims the priority of EP 06113401.1 filed May 2, 2006, the priority of both applications is hereby claimed and both applications are incorporated by reference herein.

The invention described herein relates to the use of thymosin alpha 1 (Tα1), alone or in combination with the long pentraxin PTX3 (PTX3) or one of its functional derivatives, or Ganciclovir, for the preparation of a medicament for the prevention or treatment of viral diseases and/or for inhibiting virus activation, in which said virus is selected from the group consisting of herpes virus, such as cytomegalovirus (CMV); influenza virus, such as H1N1, H3N2, H5N1 or H5N7 virus; paramixovirus, such as measles; respiratory syncytial virus; coronavirus, such as SARS; HIV Virus; hepatitis virus; or rotavirus.

Human cytomegalovirus (HCMV) is a herpesvirus commonly found in about 50% of the general population. About 90% of people with HIV carry HCMV. In the general population, the virus usually remains latent in the tissues of the body after the initial infection. It can, however, be shed in the mouth, urine, and genital tract, serving as a source of infection for other people. Infection with HCMV can result in secondary, more severe infections if the immune system becomes compromised for any reason.

Roughly 5% of infants who get HCMV through vertical transmission have serious birth defects. These can include brain damage, growth failure, blindness, and other defects. This problem usually occurs when the mother becomes infected with HCMV for the first time during pregnancy.

In the general adult population, HCMV lies dormant, but may be associated with the development of coronary artery disease. Infection with HCMV has been associated with the development of arterial plaques and atherosclerosis.

HCMV can cause serious problems in people with weakened immune systems.

This is most commonly a problem in people with AIDS or in those patients on immunosuppressive therapy. HCMV infects between 75 and 100% of HIV positive patients. The most common complications associated with HCMV include chorioretinitis; gastrointestinal tract infections, including hepatitis, esophagitis, colitis, gastritis, and pancreatitis; neurologic involvement, including encephalitis and polyradiculitis; pulmonary involvement; and epididymitis.

People with widespread cancer or people who receive organ or bone marrow transplants are commonly affected. Infection may be due to a first time exposure to HCMV or as a result of reactivated HCMV. In transplant and cancer patients, HCMV usually causes pneumonia or a gastrointestinal infection resulting in diarrhea, which may cause death. Furthermore, HCMV contributes to the development of chronic allograft dysfunction in solid organ transplant recipients. The relationship between HCMV disease and the development of bronchiolitis obliterans in lung transplant recipients is well established. Additionally, HCMV is one of a number of risk factors that may lead to allograft injury. Direct viral invasion of the allograph may cause HCMV hepatitis in liver or kidney transplant patients. In addition to direct syndromes produced by HCMV, infection with this virus may increase the risk for fungal and other opportunistic infections, such as *Pneumocystis carinii* pneumonia and Epstein-Barr virus-related post transplant lymphoproliferative disease.

Most people have been infected with HCMV by the time they are adults. Anyone receiving a blood transfusion or an organ transplant is at risk for a HCMV infection.

Furthermore, people with weakened immune systems and unborn children are at risk for severe disease.

Treating active HCMV in people with weakened immune systems is currently done with antiviral agents, such as ganciclovir, foscarnet, and cidofovir.

Influenza viruses causes flu, a contagious disease that infect the respiratory tract (nose, throat, and lungs) in humans. Influenza usually comes on suddenly and may include these symptoms: fever, headache, malaise (a feeling of being ill and without energy that can be extreme), cough, sore throat, nasal congestion and body aches.

Paramyxoviridae viruses induce a wide range of distinct clinical illnesses in humans, these include measles virus; mumps virus, which has symptoms of parotitis, orchitis and encephalitis; and the parainfluenza viruses which are respiratory pathogens.

Respiratory syncytial virus (RSV) is the most common cause of bronchiolitis and pneumonia among infants and children under 1 year of age. Illness begins most frequently with fever, runny nose, cough, and sometimes wheezing. RSV also causes repeated infections throughout life, usually associated with moderate-to-severe cold-like symptoms; however, severe lower respiratory tract disease may occur at any age, especially among the elderly or among those with compromised cardiac, pulmonary, or immune systems.

Coronaviruses infect a variety of mammals and birds, in humans they cause respiratory infections including Severe Acute Respiratory Syndrome (SARS) Enteric infections and Neurological syndromes. Adult infections are less common and re-infections appear to occur throughout life.

The Human Immunodeficiency Virus (HIV) is a retrovirus. The genetic information in a retrovirus particle is encoded by RNA. Upon entry into the host cell this RNA is copied into DNA by the virus enzyme reverse transcriptase. This cDNA copy of the virus' genetic information can integrate into the host cell chromosomes in the nucleus. This provirus can lay dormant for many cell divisions before being reactivated and producing more infectious retrovirus particles.

Viral hepatitis is any type of liver inflammation caused by a viral infection. The three most common viruses now recognized to cause liver disease are hepatitis A, hepatitis B, and hepatitis non-A, non-B (also called hepatitis C). Several other types have been recognized: hepatitis D, hepatitis E, and the recently identified hepatitis G. A seventh type (hepatitis F) is suspected but not yet confirmed.

Rotavirus is the most common cause of severe diarrhea among children, resulting in the hospitalization of approximately 55,000 children each year in the United States and the death of over 600,000 children annually worldwide.

Thymosin alpha 1 is a compound well known in the medical field.

This compound is an acidic peptides present in thymus extract which shows immunoregulatory properties in several in vitro and in vivo assay (1972; Proc. Natl. Acad. Sci. U.S.A. 69, 1800-1803).

Previous use of thymosin alpha 1 are already known.

Subcutaneous administration of thymosin alpha 1 to nude mice previously inoculated with human non-small cell lung cancer ("NSCLC") cells significantly decreased tumor volume.

Pulmonary metastases in mice with methylcholanthrene-induced fibrosarcoma were also reduced by thymosin alpha 1, and local sarcoma growth as well as liver and lung metastases of lymphosarcoma cells were significantly reduced in BALB/c mice treated with thymosin alpha 1.

PTX3 is a protein expressed in various cell types (Bottazzi, et al., J. Biol. Chem, 1997; 272; 32817-32823), particularly in mononuclear phagocytes and endothelial cells after exposure to the inflammatory cytokines Interleukin1beta (IL-1beta) and Tumor Necrosis Factor alpha (TNF-alpha).

This protein consists of two structural domains, an N-terminal unrelated to any known molecule, and a C-terminal similar to the short pentraxins such as C-reactive protein (CRP). A substantial similarity has been found between human PTX3 (hPTX3) and animal PTX3s.

The PTX3 gene is located on mouse chromosome 3, in a region similar to the human 3q region (q24-28), in keeping with the documented location of hPTX3 in the 3q 25 region. Moreover, mouse PTX3 (mPTX3) (Introna, M., et al.: Blood, 87 (1996); 1862-1872) is very similar to hPTX3 on the basis of organisation, location and sequence (Breviario, F., et al.: J. Biol. Chem., 267. 22190, 1992).

In particular, the degree of identity between the sequences is 82% between the human gene and the mouse gene, and reaches 92% if conservative substitutions are considered.

The high degree of similarity between the sequence of hPTX3 and that of mPTX3 is a sign of the high degree of conservation of pentraxin in the course of evolution (Adv. Immunol. 34: 141, 1983).

For an overview of the pentraxins, see H. Gewurz, et al., Current Opinion in Immunology, 1995, 7.54-64.

Previous use of long pentraxin PTX3 are already known.

The international patent application WO99/32516 describes the use of long pentraxin PTX3 for the therapy of infectious (fungi, bacteria, protozoa or viruses), inflammatory or tumoral diseases. In WO99/32516 it is never mentioned that PTX3 would have been useful for treating HCMV or influenza viruses.

WO02/38169 describes the use of long pentraxin PTX3 for the preparation of a medicament useful for the treatment of diseases associated with abnormal activation of growth factor FGF-2.

WO02/36151 describes the use of long pentraxin PTX3 for the treatment of autoimmune diseases.

WO03/011326 describes the use of long pentraxin PTX3 for the treatment of female infertility.

WO2005060997 describes the use of inhibitors of long pentraxin PTX3 for the preparation of a medicament for the prevention and treatment of autoimmune diseases and of degenerative diseases of bone and cartilage.

Blood, 1 Jan. 2006, Volume 107, Number 1, describes that PTX3 contributes to limit tissue damage under inflammatory conditions and the activations of autoreactive cells.

Ganciclovir is an antiviral agent well known in the medical field. It is used to treat infections caused by cytomegalovirus infection in people whose immune system is not working fully. This includes patients with acquired immune deficiency syndrome (AIDS). It is also used to help prevent CMV infection in patients who receive organ or bone marrow transplants, as well as in patients with advanced human immunodeficiency virus (HIV) infection.

Surprisingly and unexpectedly, it has now been found that thymosin alpha 1, alone or in combination with the long pentraxin PTX3 or Ganciclovir is useful for the preparation of a medicament for the inhibition of the virus activation and/or for the prevention or treatment of viral diseases.

It is therefore an object of the present invention the use of an effective amount of thymosin alpha 1, alone or in combination with the long pentraxin PTX3 or Ganciclovir, for preparing a medicament for the inhibition of the activation of virus diseases selected from the group comprising herpes virus, such as cytomegalovirus (CMV); influenza virus, such as H1N1, H3N2, H5N1 or H5N7 virus; paramixovirus, such as measles; respiratory syncytial virus; coronavirus, such as SARS: HIV Virus; hepatitis virus; or rotavirus disease; in a mammal subject.

It is a further object of the present invention the use of an effective amount of thymosin alpha 1, alone or in combination with the long pentraxin PTX3 or Ganciclovir, for preparing a medicament for the prevention and/or treatment of virus diseases selected from the group comprising herpes virus, such as cytomegalovirus (CMV); influenza virus, such as H1N1, H3N2, H5N1 or H5N7 virus; paramixovirus, such as measles, respiratory syncytial virus; coronavirus, such as SARS, HIV Virus; hepatitis virus, or rotavirus; in a mammal subject.

It is a further object of the present invention the use of an effective amount of thymosin alpha 1, alone or in combination with the long pentraxin PTX3 or Ganciclovir, for preparing a medicament for treating a cytomegalovirus induced syndrome, in which:
said syndrome is CMV mononucleosis;
said syndrome is associated with an immunocompromised host;
said immunocompromised host has AIDS;
said immunocompromised host is an organ transplant recipient.

It is a further object of the present invention the use of an effective amount of thymosin alpha 1, alone or in combination with the long pentraxin PTX3 or Ganciclovir, for preparing a medicament for treating the influenza induced syndrome, in which said syndrome is due to a virus selected from the group consisting of H1N1, H3N2, H5N1 or H5N7 virus.

The following non limiting examples illustrate the invention.

DISCUSSION OF THE DRAWINGS

FIG. 1.

Tα1 Protects from MCMV Infection In Vivo

BALB/c (FIG. 1a) and C57BL6 (FIG. 1b) mice were infected with $1\times10^5$ or $5\times10^5$ PFU of MCMV, respectively. Virus titers were quantified on MEF cells by standard plaque assay on tissues removed at different times (FIG. 1a) or a week after infection (FIG. 1b) and expressed as log 10(mean±standard errors, SE). Thymosin alpha 1 (200 µg/kg given for 7 or 14 days) and GCV (40 mg/kg given three times a week) were administered beginning the day of the infection. Controls received the scrambled peptide. Results are representative of 4 independent experiments. Bars indicate the standard errors. *P<0.05, viral load between treated and untreated mice.

FIG. 2.

Tα1 Promotes NK Cell Reactivity in MCMV Infection

Phenotypic analysis of total (FIG. 2a, FIG. 2b) or NK (FIG. 2c) cells from spleen of MCMV-infected BALB/c mice untreated (−) or treated (+) with 200 µg/kg Thymosin alpha 1 for a week; None represents uninfected mice. Numbers refer to the percentage of positive cells on FACS analysis, a week after the infection. Histograms are representative of 1 out of 4 independent experiments. (FIG. 2d) Cytotoxic activity (by standard 51Cr-release assay against YAC-1 targets) and frequency of IFN-.-producing NK cells by ELISPOT assay from mice treated as above. Bars indicate the standard errors. *P<0.05, infected vs uninfected mice. **P<0.05, Thymosin alpha 1-treated vs untreated infected mice. The results shown are from 5 independent experiments.

FIG. 3

Thymosin Alpha 1 Promotes Viral Replication, IRF7 Activation and Cytokine Production in pDC (FIG. 3a) CD11b+DC or pDC were generated from bone marrow of BALB/c mice, infected with MCMV and assessed for morphology by light microscopy and viral replication by real-time PCR of MCMV gB transcripts expression (both at 48 h) or for IRF7 nuclear expression by immunobloting with anti-IRF7 (2 h later). Cells were exposed (+) or not (−) to 50 µg/ml Thymosin alpha 1 for 2 h at 37° C. before infection. − represents uninfected cells. The results shown represent one representative experiment out of 3.

Nuclear fractionation was checked by blotting with anti-aldolase (as negative control) antibodies.

Arrow indicates an inducible band. Lane 1, uninfected cells; lane 2, MCMV-infected; lane 3, Thymosin alpha 1 treated; lane 4, MCMV+Thymosin alpha 1 treated. (FIG. 3b) Cytokine production (pg/ml) by DC subsets treated as above. Bars indicate the standard errors. *P<0.05, cytokine production in MCMV-infected DC vs uninfected DC. **P<0.05, Thymosin alpha 1-treated vs untreated DC. (FIG. 3c) Cytokine production in mice during MCMV infection. Cytokine levels (pg/ml) in culture supernatants of spleen cells from mice with MCMV infection and treated for a week with Thymosin alpha 1 or GCV. *P<0.05, treated vs untreated mice. ND, not done.

FIG. 4

Tα1 Activates the TLR9/MyD88-Dependent Pathway.

Viral load (FIG. 4a) and cytokine production (FIG. 4b) in C57BL6, TLR4-/−, TLR9-/− and MyD88-/− mice infected with 5×10$^5$ PFU of MCMV and treated with 200 µg/kg Tα1 for a week. Virus titers, expressed as log 10, were quantified on MEF cells by standard plaque assay on infected tissues removed a week after infection and treatment. Cytokine (pg/ml) levels in culture supernatants of spleen cells were determined by ELISA assay. Bars indicate the standard errors. *P<0.05, Tα1-treated vs untreated mice. Results are representative of 3 independent experiments.

FIG. 5.

Thymosin Alpha 1 is Effective in Combination with GCV.

BALB/c or C57BL6 mice were infected with 10$^5$ or 5×10$^5$ PFU of MCMV, respectively. Virus titers, expressed as log 10, were quantified on MEF cells by standard plaque assay on lung tissues removed 7 days after the infection. Tα1 (200 µg/kg/daily for a week) and/or GCV (40 mg/kg, three times a week) were administered beginning the day of the infection. Cytokine (pg/ml) levels in culture supernatants of spleen cells (7 days) were determined by ELISA assay. Bars indicate the standard errors. *P<0.05, treated vs untreated mice. Results are representative of 3 independent experiments.

FIG. 6.

Tα1 is Effective in Combination with PTX3 in Murine Cytomegalovirus Infection

Inbred C57BL6 and BALB/c mice were injected intraperitoneally (i.p.) with 1×10$^5$ (BALB/c) or 5×10$^5$ (C57BL6) plaque forming units (PFU) of MCMV. Virus titers were quantified on MEF cells by standard plaque assay on tissues removed a day after treatment. Treatments were as follow: Tα1 (200 mg/kg/ip) and PTX3 (1 mg/k/ip) (SIGMA-Tau, Pomezia, Rome, Italy) were given daily for 7 consecutive days beginning the day of the infection. Controls received the scrambled peptide. All organs from uninfected animals were negative viruses. Virus titers are expressed as log 10 (mean±standard errors, SE).

EXAMPLE 1

Materials and Methods

Mice. Wild-type (WT) inbred C57BL6 and BALB/c mice, 8 to 12 weeks old, were purchased from Charles River Breeding Laboratories (Calco, Italy). Pairs of homozygous TLR9-(TLR9-/−), TLR4-(TLR4-/−), and MyD88-(MyD88-/−)-deficient mice (on the C57BL6 background), were bred under specific pathogen-free conditions at the breeding facilities of the University of Perugia, Perugia, Italy. Experiments were performed following protocols approved by the institutional animal committee and in accordance with European Economic Community Council Directive as well as institutional animal care and use guidelines.

Virus, infection and treatments. Stocks of Smith strain MCMV salivary gland extracts were prepared from BALB/c mice and titered in a standard plaque assay on BALB/c murine embryonic fibroblast (MEF) cells (J. Gen. Virol. 2002; 83:2983-2993). Mice were injected intraperitoneally (i.p.) with 1×10$^5$ (C57BL6) plaque forming units (PFU) of MCMV. Virus titers were quantified on MEF cells by standard plaque assay on tissues removed at different times. Treatments were as follows: Thymosin alpha 1 and the scrambled polypeptide (both from SciClone Pharmaceuticals, San Mateo, CA) were supplied as purified (the endotoxin levels were <0.03 pg/ml, by a standard limulus lysate assay) sterile, lyophilized, acetylated polypeptide. The sequences were as follows: Ac-Ser-Asp-Ala-Ala-Val-Asp-Thr-Ser-Ser-Glu -Ile-Thr-Thr-Lys-Asp-Leu-Lys-Glu-Lys-Lys-Glu-Val-Glu-Glu-Ala-Glu-Asn-O (Tα1) SEQ ID NO:1 and Ac-Ala-Lys-Ser-Asp-Val-Lys-Ala-Glu-Thr-Ser-Ser-Glu-Ile-Asp-Thr-Thr-Glu-Leu -Asp-Glu-Lys-Val-Glu-Val-Lys-Ala-Asn-Glu-OH (scrambled peptide) SEQ ID NO:2. The lyophilized powders were reconstituted in sterile water and 200 µg/kg/i.p. were given daily for 7 or 14 consecutive days beginning the day of the infection. Gancyclovir (GCV) (Cymevene; from Recordati, Milan, Italy) was administered at 40 mg/kg/i.p. three times a week, every other day, beginning 6 h after infection. Controls received the scrambled peptide or the diluent alone.

DC subset generation. DC were obtained by culturing 10$^6$/ml BALB/c bone marrow cells in Iscove's modified medium, containing 10% filtered bovine serum, 50 µM 2-mercaptoethanol, sodium pyruvate (1 mM), 2 mM L-glutamine, HEPES (10 mM), and 50 µg/ml gentamycin in the presence of 150 U/ml mouse rGM-CSF (Sigma) and 75 U/ml rIL-4 (R&D Systems) for 7 days to obtain CD11b+DC or 200 ng/ml FLT3-L (Immunex Corporation, Seattle, Wash.) for 9 days to obtain pDC. Final maturation was accomplished by the addition of 1 µg/ml LPS or 2 µg/ml cytosine phosphorothioateguanine oligodeoxynucleotide (CpG-B ODN 1668) (Coley Pharmaceutical Group, Wellesley, Mass.) for additional 24 h to CD11b+DC or pDC, respectively (Blood 2003; 102: 3807-3814) CD11b+DC were discriminated on CD11chigh expression and were distinctly composed of CD8a+DC and CD11b+DC. pDC were defined as CD11clow, Ly6C+, CD8a+/− cells. Photographs were taken using a high Resolution Microscopy Color Camera AxioCam, using the AxioVision Software Rel. 3.1 (Carl Zeiss S.p.A., Milano, Italy).

Flow cytometry analyses. After blocking of FcRs with the anti-CD16/32 (2.4G2) antibody, cells were analyzed for antigen expression with a FACScan flow cytofluorometer (Becton Dickinson, Mountain View, Calif.) equipped with CELLQuest™ software. Control staining of cells with irrelevant Ab was used to obtain background fluorescence values. Abs were from PharMingen.

Plaque assay. Plaque assay was determined on cells grown to subconfluence and incubated with serially diluted virus samples for 2 h at 37° C. (10). All organs from uninfected animals were negative viruses. Virus titers are expressed as log 10 (mean±standard errors, SE).

Inhibition of viral replication. DC ($10^6$/well) were pre-incubated for 2 h at 37° C. with 50 µg/ml thymosin alpha 1 diluted in serum-free DMEM and then added of $10^5$ PFU MCMV. Infectivity was measured 48 h later.

NK cell cytotoxic activity. NK cells, purified from spleens by DX5 microbeads (Miltenyi Biotec), were defined as NK1.1+CD3-cells. NK cytolytic activity was assessed against 51 Cr-labeled YAC-1 lymphoma cells (Blood 2005; 106:4397-4406).

Immunoblot analysis of IRF7. DC were exposed for 2 to 50 µg/ml Thymosin alpha 1 or $10^5$ PFU MCMV, either alone or in combination. Nuclear extracts were prepared with NE-PER nuclear and cytoplasmic extraction reagents (Pierce, Celbio S.r.l., Milan, Italy) and the protein concentration of the nuclear extracts was determined with a BCA-200 protein assay kit (Pierce) following the manufacture's instructions. Nuclear content of IRF7 was determined by Western blot using rabbit anti-IRF7 (H246) antibody and bovine anti-rabbit-horseradish peroxidase (Santa Cruz Biotechnology). Visualization was performed with the ECL Western blotting analysis system from Amersham and Kodak Biomax films.

Real time RT-PCR for quantification of MCMV mRNA. A highly sensitive RT-PCR assay was used for amplification of the 356-bp segment of MCMV glycoprotein B (gB) DNA from total cellular RNA (51). Synthesis and PCR of cDNA were done as described (Blood 2003; 102-3807-344 3814). Synthetic DNA oligonucleotide primers were selected from the published sequence of the MCMV gB gene (17). The sense primer was based on the cDNA No. 2416-2443:5'-AAG-CAG-CAC-ATC-CGC-ACC-CTG-AGC-GCC-3' SEQ ID NO:3, and the antisense on No. 2745-2772: 5'-CCA-GGC-GCT-CCC-GGC-GGC-CCG-CTC-TCG-3' SEQ ID NO:4, Cycling conditions were initial denaturation for 3 min at 95° C., 1 min at 50° C., and 20 s at 72° C., and a final extension for 10 min at 72° C. PCR amplification of the housekeeping β-actin gene was performed for each sample to control for sample loading and allow normalization between samples as per manufacturer's instructions (Applied Biosystems).

Quantification of cytokines by ELISA and ELISPOT assays. The levels of cytokines in the culture supernatants of mitogen-stimulated spleen cells (48 h stimulation with 10 µg/ml ConA) or MCMV-pulsed DC (24 h) were determined by ELISA (R&D Systems and PBL, Biomedical Lab, Milan, Italy). The detection limits (pg/ml) of the assays were <16 for IL-12 p70, <10 for IFN-., <3 for IL-10 and <10 for IFN-a. IFN-.-producing NK cells were enumerated by ELISPOT assay on purified NK (Virus Res. 2003; 98:17-467 25). Results are expressed as the mean number of cytokine-producing cells (±SE) per $10^5$ cells, calculated using replicates of serial 2-fold dilutions of cells.

Statistical analyses. Student's paired t test was used to determine the significance of values in experimental groups (significance was defined as P<0.05). Survival data were analyzed using the Mann-Whitney U test. In vivo groups consisted of 6 animals. Unless otherwise indicated, data are mean±SE.

Results

Figure 1:
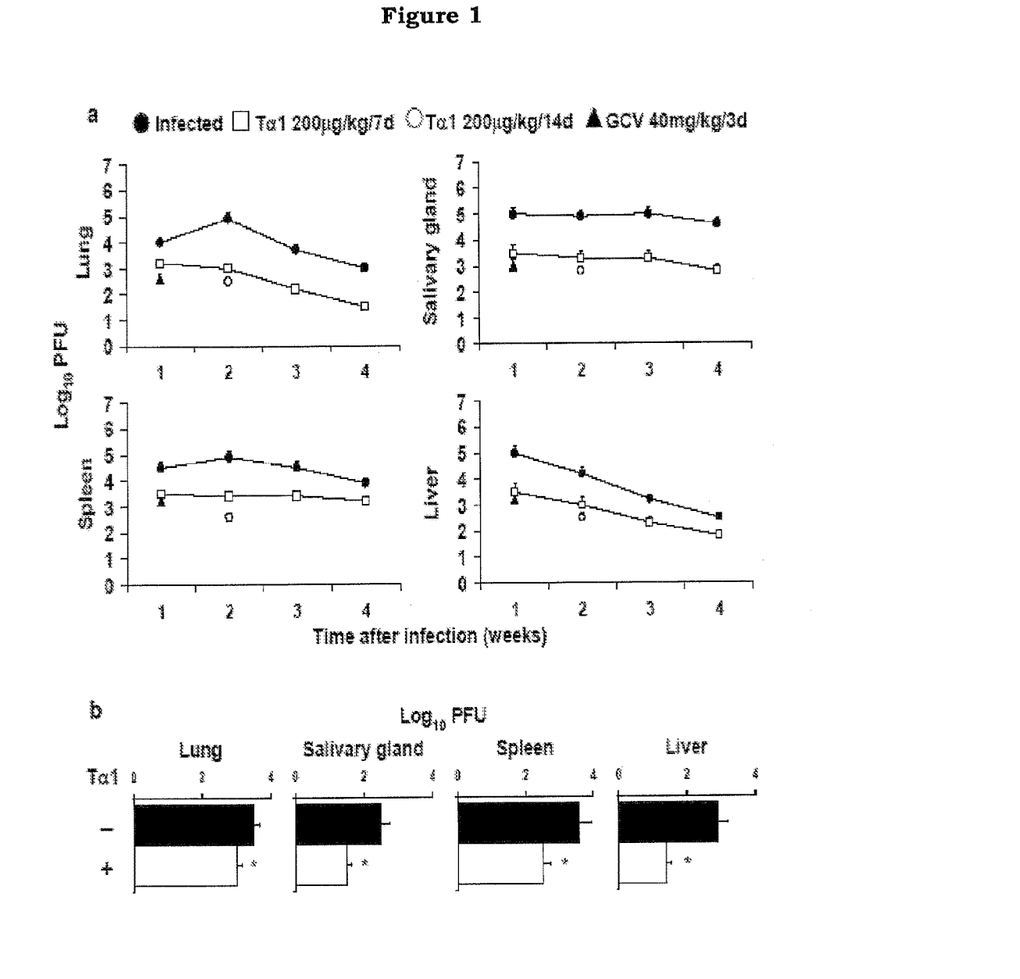

Thymosin alpha 1 protects from MCMV infection. The effects of Thymosin alpha 1 administration in the acute primary MCMV infection of either susceptible (BALB/c) or resistant (C57BL6) mice was assessed. Mice were infected with a sublethal dose of MCMV, treated with Thymosin alpha 1 or GCV and the titer loads in spleen, lung, liver and salivary gland were determined at different weeks after the infection by standard plaque assay titration. MCMV replicated to higher titers in the visceral organs of susceptible (FIG. 1a) than resistant (FIG. 1b) mice, particularly in the early phase of the infection. Thymosin alpha 1, given at 200 µg/kg for 7 days, but not the scrambled peptide, significantly decreased the viral load in different visceral organs, in both susceptible and resistant mice. The effect was similar to that of GCV and was higher with Thymosin alpha 1 given for 14 days. In resistant mice, the effect of Thymosin alpha 1 was particularly evident in the salivary gland and liver (FIG. 1b). Thymosin alpha 1 also significantly decreased the viral load in BALB/c mice infected with a higher PFU (data not shown). These results are the demonstration that Thymosin alpha 1 exerts a therapeutic effects in MCMV infection.

Figure 2:
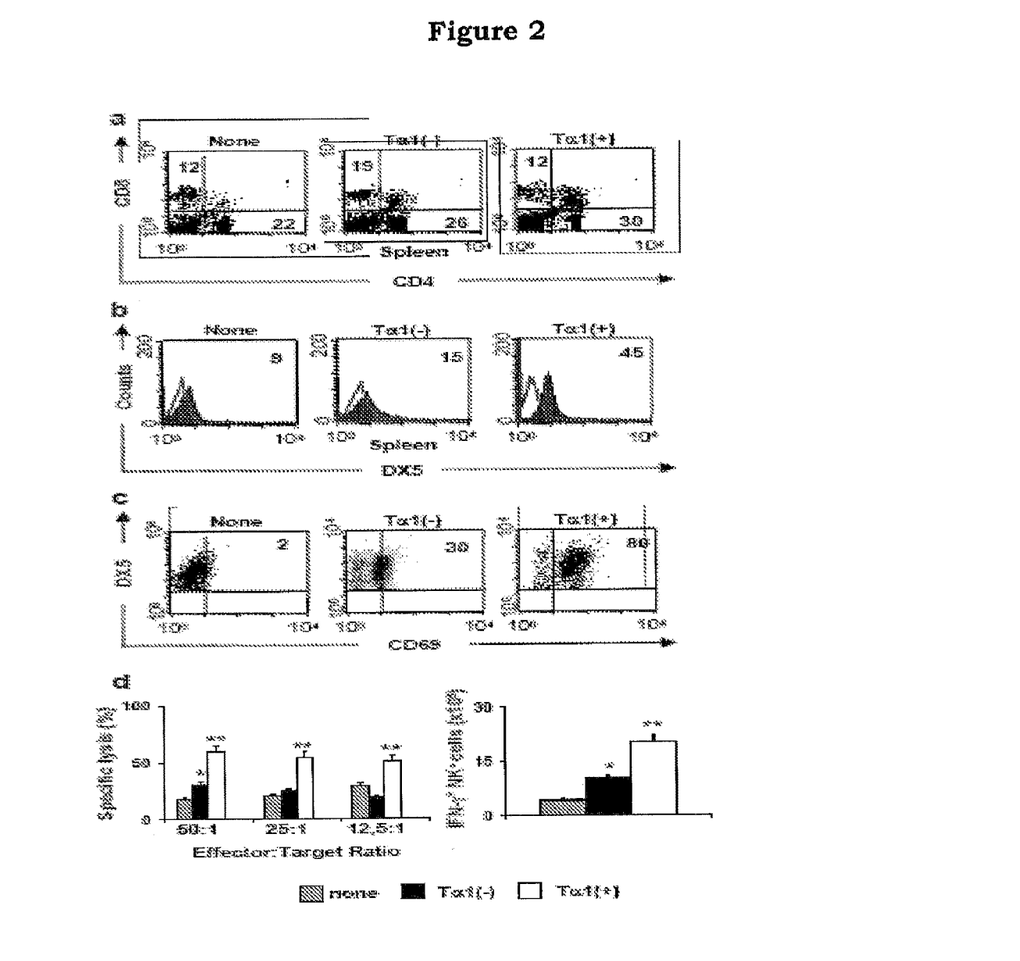

Thymosin alpha 1 recovers NK reactivity and promotes cytokine production in MCMV infection. Ly49H NK cells are pivotally involved in the control of MCMV infection through different mechanisms, including the reciprocal regulation of CD8a+DC (4). The effect of Thymosin alpha 1 on the expansion and functional activity of NK cells in the spleen of MCMV-infected mice was evaluated. FIG. 2 shows that a week treatment with Thymosin alpha 1, while not affecting the expansion of CD4+ or CD8+ T cells (FIG. 2a), expanded NK1.1+ NK cells (FIG. 2b). NK cells were fully activated as revealed by the increased expression of the activation marker CD69 (FIG. 2c). The frequency of IFN-.-producing cells and cytotoxic activity of ex-vivo purified splenic NK cells were also both significantly up-regulated upon thymosin alpha 1 treatment (FIG. 2d).

Figure 3:
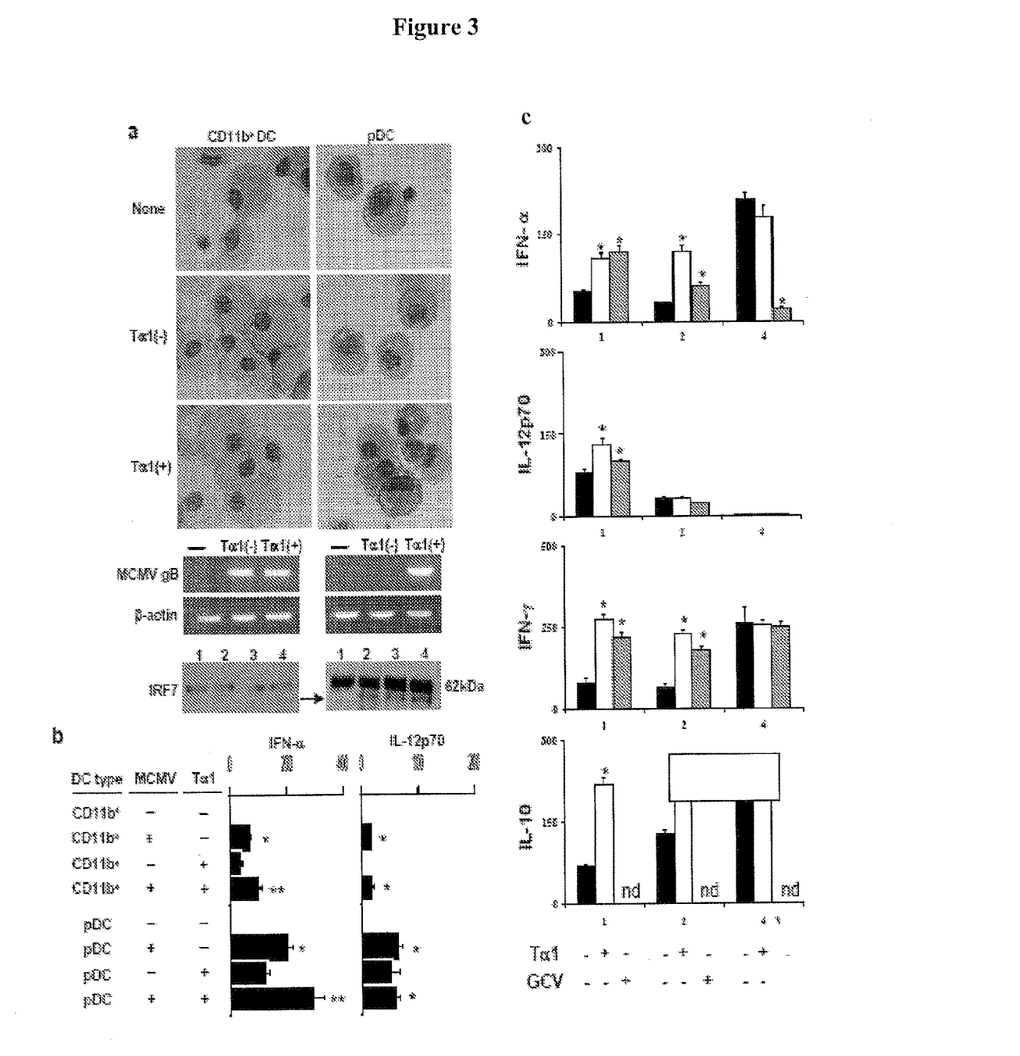

Thymosin alpha 1 promotes viral infection, IRF7 activation and cytokine production in pDC. As early activation of NK cells in MCMV infection is mediated by IFN-a/β which promotes cytotoxicity and proliferation of NK cells, and IL-12 which induces IFN-. production (Nat. Immunol. 2001; 2: 1144-1150; An. J. Immunol. 1996; 156:1138-1142), the pattern of cytokine production by DC subsets exposed to MCMV in the presence of thymosin alpha 1 was evaluated. Acute infection with MCMV induced a transient, but profound, immunosuppression in susceptible BALB/c mice, which can be linked to infection of CD11b+DC (Nat. Immunol. 2001; 2: 1077-1084). CD11b+DC support productive infection of MCMV both in vitro and in vivo (Nat. Immunol. 2001; 2:1077-1084), whereas MCMV does not replicate in pDC (J. Exp. Med. 2003; 197:885-898; J. Exp. Med. 2002; 195:517-528). To bone marrow-derived CD11b+DC or pDC subsets from uninfected mice was resorted and was directly assessed the effect of Thymosin alpha 1 on cytokine production by and viral replication in the different DC subsets. In line with previous studies (Nat. Immunol. 2001; 2: 1077-1084; Proc. Natl. Acad. Sci. USA 2004; 101:3516-3521), MCMV replicated in CD11b+DC but not in pDC. Interestingly, viral replication was not affected by Thymosin alpha 1 in CD11b+DC but was actually promoted in pDC (FIG. 3a). It is known that HCMV elicits a coordinated cellular antiviral response for interferon production which includes the temporal activation of IRF3 and IRF7 that results in nuclear accumulation of these factors. As IRF7 is the master regulator of antiviral type 1 IFN production in pDC, the levels of nuclear IRF7 expression in both DC subsets upon virus and/or Thymosin alpha 1 exposure by immunoblotting with anti-IRF7 antibody were measured. It was noted translocation of IRF7 upon either virus or Thymosin alpha 1 exposure, either alone or in combination in pDC but not in CD11b+DC (FIG. 3a). It was also assessed IRF3 phosphorylation and translocation and was found it activated in CD11b+DC upon viral exposure alone or together with Thymosin alpha 1 but not detected in pDC (data not shown). In terms of cytokine production, both DC subsets produced IFN-a and IL-12p70 in response to the virus, as already known, although pDC more than CD11b+DC. However, pre-treatment of pDC with Thymosin alpha 1 greatly increased the production of IFN-a, while not affecting that of IL-12p70. Interestingly enough, Thymosin alpha 1 slightly promoted IFN-a by CD11b+DC (FIG. 3b). These data are the demonstration that Thymosin alpha 1 promotes the IRF7-dependent antiviral program in pDC. To correlate the pattern of cytokine production in vitro with that occurring in vivo, IL-12p70, IFN-a, IFN- and IL-10 production in culture supernatants of spleen cells from BALB/c mice with MCMV infection and treated with Thymosin alpha 1 was measured. It was found that treatment with Thymosin alpha 1 significantly increased IFN-a and IFN-. productions, particularly in the first weeks of the infection. IL-12p70 was also slightly increased soon after treatment, to decline thereafter. These effects were comparable to those obtained with GCV. Interestingly, Thymosin alpha 1 also dramatically increased IL-10 production (FIG. 3c). Together, these data shown that thymosin alpha 1 favours the activation of the IFN-a/IFN209.-dependent pathway in response to MCMV.

Figure 4:
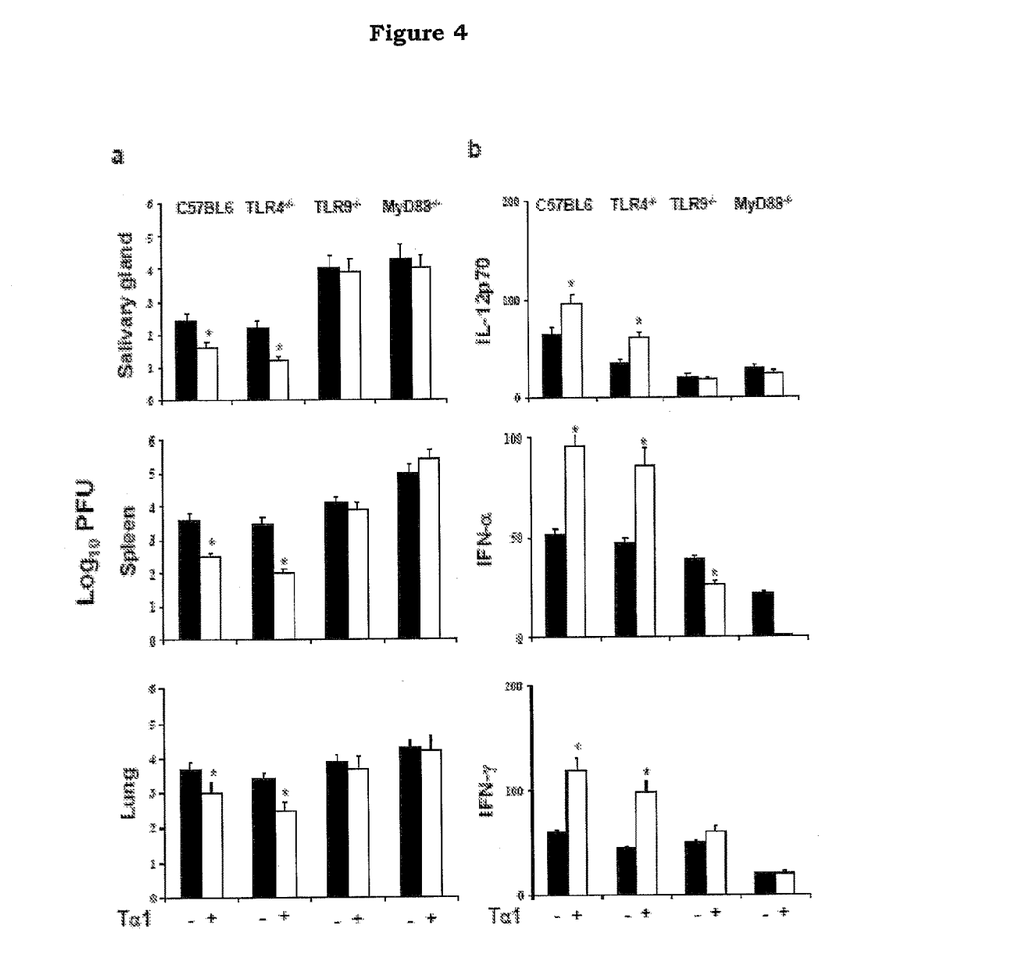
Figure 5:
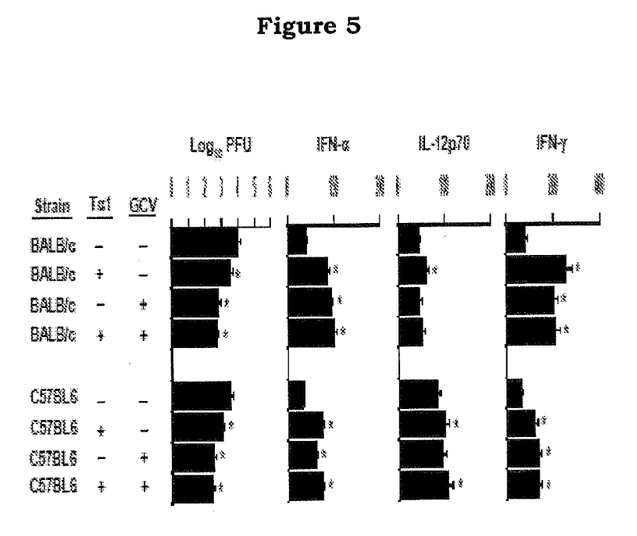

Thymosin alpha 1 activates the TLR9/MyD88-dependent pathway. Effective anti-MCMV immune surveillance required functional TLR signals, in particular the TLR9/MyD88 signalling pathway has a crucial role for the IRF7-dependent antiviral program (27) and a rapid MCMV clearance, whereas TLR2, TLR3, and TLR4 did not seem to play a significant role (J. Immunol. 2005; 175:6723-6732). To assess the involvement of TLR in the effect of Thymosin alpha 1 in the infection, TLR-deficient mice were challenged with MCMV, treated with Thymosin alpha 1 and followed for viral replication. In accordance with published data (J. Immunol. 2005; 175:6723-6732), TLR9-/- and, particularly, MyD88-/- mice were more susceptible to MCMV than C57BL6 mice, while deficiency for TLR4 did not significantly affect mouse resistance (FIG. 4a). Thymosin alpha 1 was effective in C57BL6 and in TLR4-/- mice but completely ineffective in TLR9-/- and MyD88-/- mice, a finding suggesting the involvement of the TLR9/MyD88-dependent signaling in the antiviral activity of thymosin alpha 1. Here again, the efficacy of thymosin alpha 1 directly correlated with the production of IFN-α, more than IL-12p70, and IFN-. whose levels were significantly increased in supernatants of splenocytes from C57BL6 and TLR4-/- mice, but not TLR9-/- or MyD88-/- mice (FIG. 4b).

EXAMPLE 2

Thymosin Alpha 1 is Synergistic in Combination with GCV

Using the methods described in Example 1, was assessed whether Thymosin alpha 1 could work in combination with GCV. To this purpose, susceptible or resistant mice infected with MCMV were concomitantly treated for a week with GCV and/or Thymosin alpha 1 and assessed for viral titers and patterns of cytokine production. Preliminary results obtained shown that this combination is synergistic in decreasing the viral titers in the lung of either type of mice and promoted the production of IFN-α and IFN-. T.

EXAMPLE 3

Thymosin Alpha 1 is Synergistic in Combination with PTX3

Using the methods described in Example 1, was assessed whether Thymosin alpha 1 could work in combination with PTX3.

Figure 6:
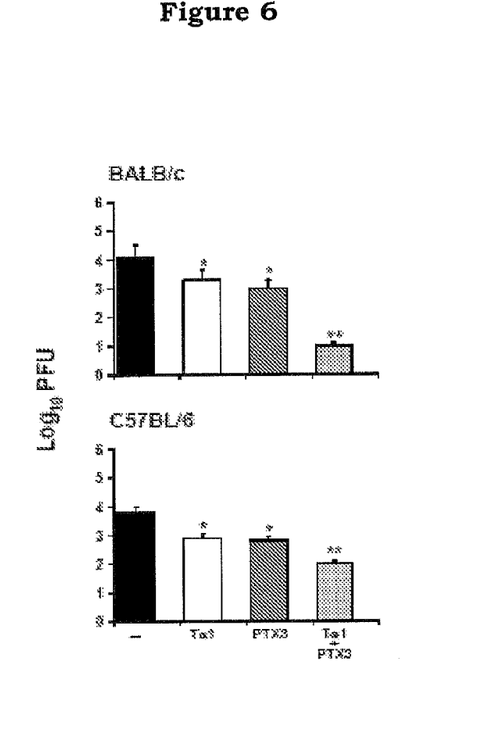

To this purpose, susceptible (BALB/c) or resistant (C57BL6) mice infected with MCMV were concomitantly treated for a week with PTX3 and/or Thymosin alpha 1 and assessed for viral titers in the lungs. The results (FIG. 6) confirmed that either agent alone decreased the viral titers in the lung of either type of mice. Moreover, surprisingly in either susceptible or resistant mice, the combination of the active ingredients exhibited an unexpected synergism, in terms of restriction of viral replication and in terms of production of IFN-a and IFN-g, IL-12p70 and IFN-g.

The present invention contemplates a therapeutic package for dispensing to, or for use in dispensing to, a patient being treated for a viral disease (or for the inhibition of the activation of the virus) comprising one or more unit doses, each unit dose comprising an amount of thymosin alpha 1, and optionally an amount of the long pentraxin PTX3 or Ganciclovir therein such that periodic administration of one or more of said unit doses is effective to treat, for example, HCMV; and a finished pharmaceutical container therefore, said container further containing or comprising labeling, said labeling indicating that thymosin alpha 1, and optionally the long pentraxin PTX3 or Ganciclovir, is indicated for the treatment of patients with, for example, HCMV.

Additionally, the present invention contemplates an article of manufacture comprising packaging material and thymosin alpha 1, and optionally the long pentraxin PTX3 or Ganciclovir, contained within said packaging material, wherein the long pentraxin PTX3 is therapeutically effective for treating HCMV, and wherein the packaging material comprises a label which indicates that the long pentraxin PTX3 can be used to treat HCMV.

According to the present invention thymosin alpha 1 and optionally the long pentraxin PTX3 or Ganciclovir may be administered in a separate form or in the form of an unitary dosage comprising the active ingredients and optionally diluent or excipients pharmaceutically acceptable.

According to the present invention when thymosin alpha 1 and the long pentraxin PTX3 or Ganciclovir are administered in a separate form (i.e. 2 different administration), said active ingredients may be administered sequentially (i.e. in the same moment) or sequentially according to a schedule suggested in the labeling above mentioned.

In the use according to the invention, the terms "treat" or "treating" bear their usual meaning which includes preventing, prohibiting, alleviating, inhibiting, ameliorating, halting, restraining, slowing or reversing the progression, activation or reduction of the severity of a viral disease.

In the use according to the invention, the term "effective amount" refers to an amount of the compound, which is capable of performing the intended result. For example, an effective amount of thymosin alpha 1, and optionally the long pentraxin PTX3 or Ganciclovir that is administered in an effort to treat a viral disease is that amount which is required to prevent, prohibit, alleviate, ameliorate, halt, restrain, slow or reverse the progression, or reduce the severity of said viral disease, and the daily dose to be administered will depend, according to the judgement of the primary care physician, on the subject's weight, age and general condition of the patient.

The present invention also includes methods employing pharmaceutical formulations, which contain, as the active ingredient, thymosin alpha 1, and optionally the long pentraxin PTX3 or Ganciclovir, in association with pharmaceutical carriers. A skilled artisan would know of such formulations and their manufacture, see, e.g., REMINGTON'S PHARMACEUTICAL SCIENCES, (16th ed. 1980).

The formulations are preferably formulated in a unit dosage form of the active ingredient. The term "unit dosage form" refers to physically discrete units suitable as unitary dosages for human subjects, each unit containing a predetermined quantity of thymosin alpha 1, and optionally the long pentraxin PTX3 or Ganciclovir, calculated to produce the desired therapeutic effect, in association with a suitable pharmaceutical excipient.

Thymosin alpha 1, and optionally the long pentraxin PTX3 or Ganciclovir can be administered in the form of a pharmaceutical composition in combination with pharmaceutically acceptable carriers or excipients, the proportion and nature of which are determined by the solubility and chemical properties of the compound in the carriers and/or excipients selected, the chosen route of administration, and standard pharmaceutical practice.

Pharmaceutical compositions are prepared in a manner well known in the pharmaceutical art see, e.g., REMINGTON'S PHARMACEUTICAL SCIENCES, (16th ed. 1980). The carrier or excipient may be a solid, semi-solid, or liquid material, which can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solution, suspensions, liposome or the like.

The invention claimed is:

1. A method of treating herpes virus diseases in a mammal subject, comprising
    administering an effective amount of thymosin alpha 1 in combination with long pentraxin PTX3 to a mammal subject in need thereof; and
    treating said herpes virus diseases in said mammal subject.

2. Method of claim 1, wherein said herpes virus is cytomegalovirus (CMV).

3. Method of claim 1 for treating a cytomegalovirus induced syndrome, wherein:
    said syndrome is CMV mononucleosis;
    said syndrome is associated with an immunocompromised host;
    said immunocompromised host has AIDS; and
    said immunocompromised host is an organ transplant recipient.

* * * * *